(12) United States Patent
Maillet et al.

(10) Patent No.: US 12,702,503 B2
(45) Date of Patent: Aug. 11, 2026

(54) SURGICAL ROBOTIC ARM WITH PROXIMITY SKIN SENSING

(71) Applicant: ORTHOSOFT ULC, Montreal (CA)

(72) Inventors: Pierre Maillet, Mudaison (FR); Patrice Bonaric, Saint Georges d'Orques (FR); Maxence Francois, Montpellier (FR); Laurent Ricatti, Candillargues (FR)

(73) Assignee: ORTHOSOFT ULC, Montreal (CA)

( * ) Notice: Subject to any disclaimer, the term of this patent is extended or adjusted under 35 U.S.C. 154(b) by 155 days.

(21) Appl. No.: 18/647,034

(22) Filed: Apr. 26, 2024

(65) Prior Publication Data

US 2024/0358454 A1 Oct. 31, 2024

Related U.S. Application Data

(60) Provisional application No. 63/498,542, filed on Apr. 27, 2023.

(51) Int. Cl.
*A61B 34/30* (2016.01)
*A61B 34/10* (2016.01)
*A61B 34/20* (2016.01)

(52) U.S. Cl.
CPC ........ *A61B 34/30* (2016.02); *A61B 2034/102* (2016.02); *A61B 2034/2055* (2016.02)

(58) Field of Classification Search
CPC .............. A61B 34/30; A61B 2034/105; A61B 2034/102; A61B 2034/2055
See application file for complete search history.

(56) References Cited

U.S. PATENT DOCUMENTS

| | | | | |
|---|---|---|---|---|
| 2010/0061509 | A1 | 3/2010 | D'Ambrosio et al. | |
| 2016/0361125 | A1* | 12/2016 | Balicki | A61B 34/30 |
| 2019/0328470 | A1* | 10/2019 | Tojo | A61B 34/25 |
| 2020/0078097 | A1* | 3/2020 | Gregerson | B25J 9/1666 |
| 2021/0178605 | A1 | 6/2021 | Shigetaka | |
| 2023/0107307 | A1 | 4/2023 | Liu et al. | |

OTHER PUBLICATIONS

Y. Ye, C. Zhang, C. He, X. Wang, J. Huang and J. Deng, "A Review on Applications of Capacitive Displacement Sensing for Capacitive Proximity Sensor," in IEEE Access, vol. 8, pp. 45325-45342, 2020 (Year: 2020).*

Sensation Technology by FOGALE nanotech Video https://www.youtube.com/watch?v=iQml1YANjSc.

* cited by examiner

*Primary Examiner* — Chao Sheng
(74) *Attorney, Agent, or Firm* — NORTON ROSE FULBRIGHT CANADA LLP

(57) ABSTRACT

A robotized computer-assisted surgery system may include a processing unit and a non-transitory computer-readable memory communicatively coupled to the processing unit and comprising computer-readable program instructions executable by the processing unit for obtaining readings from some capacitive sensors representative of at least one object within range; generating a surface model of the at least one object from the readings; and continuously tracking and outputting the position and orientation of the at least one object relative to the robot arm, using the readings and the surface model.

19 Claims, 3 Drawing Sheets

SURGICAL ROBOTIC ARM WITH PROXIMITY SKIN SENSING

CROSS-REFERENCE TO RELATED APPLICATION

The present application claims the priority of U.S. Patent Application No. 63/498,542, filed on Apr. 27, 2023, incorporated herein by reference.

TECHNICAL FIELD

The present application relates to bone and tool tracking in robotized computer-assisted surgery.

BACKGROUND OF THE ART

Robot arms have become prominent equipment in surgical rooms, often in assistance to operating staff, or as being the main tool manipulating device. In a particular application, commonly but not exclusively used in orthopedic surgery, the robot arm supports instruments, e.g., known as guides, relative to a body part of a patient, while the operating staff such as a surgeon manipulates the tools using the guides to perform bone alterations. The characteristics of a robot arm, such as its stiffness and capacity to hold its position and orientation, combined with the precision of robot arm position tracking, may benefit the operating staff and the patient by contributing to the success of a surgical procedure.

The surgical robot arms may be used in conjunction with a tracking system. Tracking of the robot arm, surgical instruments or tools and bodily parts is an integral part of computer-assisted surgery (hereinafter "CAS"). The tools are tracked for position and/or orientation in such a way that information relating the tools to bodily parts is obtained. The information is then used in various interventions (e.g., orthopedic surgery, neurological surgery) with respect to the body, such as bone alterations, implant positioning, incisions and the like during surgery.

The tracking technologies may use different technologies, such as mechanical, acoustical (ultrasound), magnetic, optical and radio frequency (RF) tracking. Depending on the technology used, different types of trackable members are fixed, permanently or temporarily, to the items that needs to be tracked. For instance, during Total Knee Replacement (TKR) surgery, trackable members are fixed to the limbs and to the different surgical instruments, and these trackable members are tracked by the tracking system. The CAS system calculates position and orientation data associated with the tracking, and the information displayed by the computer is used by the surgeon to visualize the position of the instrument(s) being manipulated with respect to the limbs, or in numerical values.

Optical tracking is commonly used in different forms. For example, passive retroreflective components are provided on tools and bones. In order to obtain values for position and/or orientation, the optical elements must be in the line of sight of the optical sensor device. One common constraint with optical tracking systems is the requirement for a line of sight between image acquisition devices stationary and the objects to track. A surgical procedure employing optical tracking may be imposed a given orientation as a function of the required visibility between the optical sensor apparatus and the optical elements. If the line of sight is disrupted, tracking may be paused, as a possible consequence. In automated robotic surgery, the interruption of optical tracking may result in the need for human intervention. There remains room for improvement.

SUMMARY

In accordance with an aspect of the present disclosure, there is provided a robotized computer-assisted surgery system, comprising: a robot arm; an in-robot sensor system in the robot arm, the in-robot robot system having a plurality of capacitive sensors; a processing unit; and a non-transitory computer-readable memory communicatively coupled to the processing unit and comprising computer-readable program instructions executable by the processing unit for: obtaining readings from at least some of the capacitive sensors representative of at least one object within range; generating a surface model of the at least one object from the readings; and continuously tracking and outputting the position and orientation of the at least one object relative to the robot arm, using the readings and the surface model.

Further in accordance with the aspect, for instance, the computer-readable program instructions are executable by the processing unit for controlling movements of the robot arm as a function of a position and orientation of the surface model of the at least one object.

Still further in accordance with the aspect, for instance, the system performs the continuously tracking and outputting the position and orientation solely with the in-robot sensor system.

Still further in accordance with the aspect, for instance, the system includes a tracker device for optically tracking the at least one object and the robot arm, the system performing the continuously tracking and outputting the position and orientation with the in-robot sensor system and with readings from the tracker device.

Still further in accordance with the aspect, for instance, the system outputs an image of the surface model of the object.

Still further in accordance with the aspect, for instance, the system outputs an image of a tool supported by the robot arm relative to the image of the surface model of the object.

Still further in accordance with the aspect, for instance, the plurality of capacitive sensors are concealed within the robot arm.

Still further in accordance with the aspect, for instance, the at least object is at least one anatomical part of a patient.

Still further in accordance with the aspect, for instance, the system blocks movement of the robot arm to avoid contact with the at least one object, using the tracking of the surface model of the object.

In accordance with another aspect of the present disclosure, there is provided a robotized computer-assisted surgery system, comprising: a robot arm; an in-robot sensor system in the robot arm, the in-robot robot system having a plurality of capacitive sensors; a processing unit; and a non-transitory computer-readable memory communicatively coupled to the processing unit and comprising computer-readable program instructions executable by the processing unit for: obtaining readings from at least some of the capacitive sensors representative of at least one object within range of the capacitive sensors; processing the readings to determine a location of the at least one object relative to the robot arm; and triggering a user interaction with the robotized computer-assisted surgery system when the object is at a given location relative to the robot arm.

Further in accordance with the other aspect, for instance, the computer-readable program instructions are executable by the processing unit for triggering the user interaction with the robotized computer-assisted surgery system when the object is within a proximity distance of part of the robot arm.

Still further in accordance with the other aspect, for instance, the computer-readable program instructions are executable by the processing unit for triggering the user interaction when the object is within a proximity distance to a passive visual indicator on the robot arm.

Still further in accordance with the other aspect, for instance, the computer-readable program instructions are executable by the processing unit for triggering the user interaction when the object touches the passive visual indicator on the robot arm.

Still further in accordance with the other aspect, for instance, at least two of the passive visual indicator are provided.

Still further in accordance with the other aspect, for instance, the computer-readable program instructions are executable by the processing unit for triggering the user interaction of a first type when the object is within a proximity distance to a first of the passive visual indicators, and for triggering the user interaction of a second type when the object is within a proximity distance to a second of the passive visual indicators.

Still further in accordance with the other aspect, for instance, the computer-readable program instructions are executable by the processing unit for programming a type of interaction associated with the passive virtual indicator.

Still further in accordance with the other aspect, for instance, the computer-readable program instructions are executable by the processing unit for triggering the user interaction by activating a collaborative mode, in which the robot arm moves based on movements of the operator as detected by some of the capacitive sensors.

Still further in accordance with the other aspect, for instance, the computer-readable program instructions are executable by the processing unit for triggering the user interaction as a movement of a mouse on a pad by the object moving relative to a given zone of the robot arm.

Still further in accordance with the other aspect, for instance, the object is a user's hand.

Still further in accordance with the aspect, for instance, the plurality of capacitive sensors are concealed within the robot arm.

DETAILED DESCRIPTION

Figure 1:
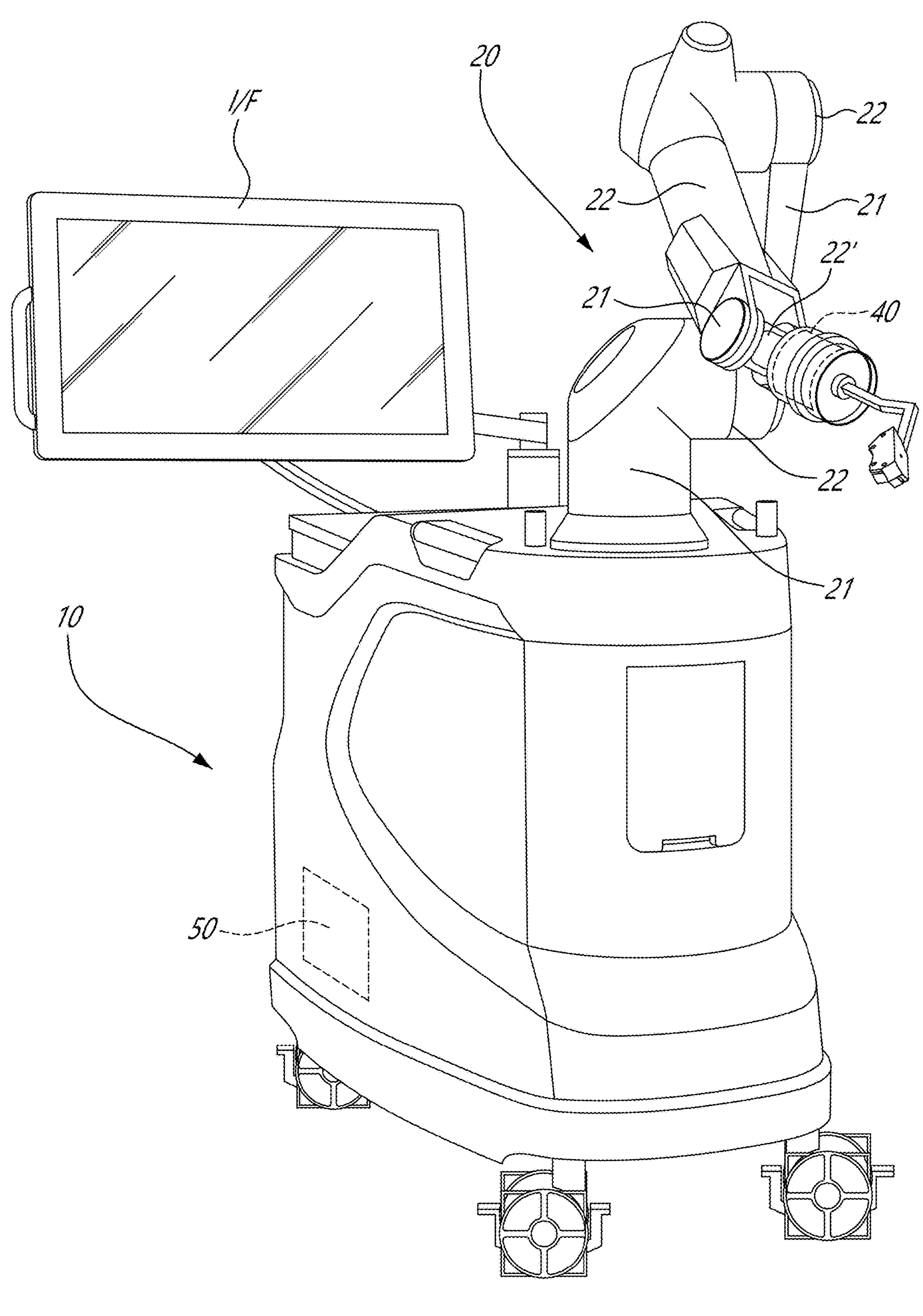
FIG. 1 is a schematic view of a surgical robot with proximity skin sensing in accordance with an aspect of the present disclosure.
Figure 2:
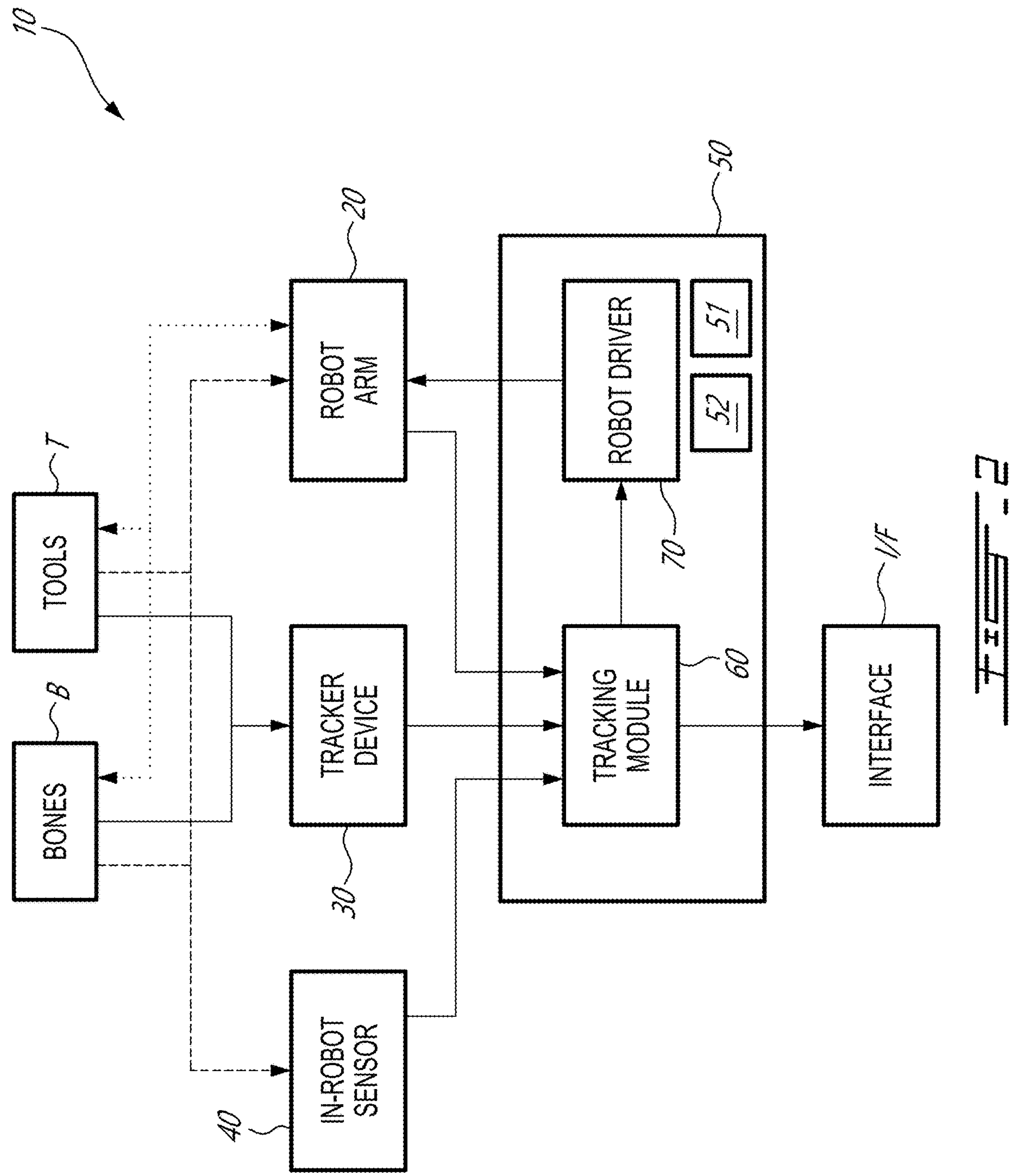
FIG. 2 is a block diagram of a computer-assisted surgery system featuring the surgical robot of FIG. 1.

Referring to FIGS. 1 and 2, a robotized computer-assisted surgery (CAS) system is generally shown at 10, and is used to provide surgery assistance to an operator. In FIG. 1, the system 10 is shown relative to a dummy patient's knee joint in supine decubitus, but only as an example. The system 10 could be used for other body parts, including non-exhaustively hip joint, spine, and shoulder bones, for orthopedic surgery, but could also be used in other types of surgery.

The robotized CAS system 10 may include a robot as shown by its one or more robot arms 20, a tracker device 30, an in-robot sensor system 40, a CAS controller 50, a tracking module 60, and a robot driver module 70, or any combination thereof:

- The robot, shown by its robot arm 20 may be present as the working end of the system 10, and may be used to perform or guide bone alterations as planned by an operator and/or the CAS controller 50 and as controlled by the CAS controller 50. The robot arm 20 may also be configured for collaborative/cooperative mode in which the operator may manipulate the robot arm 20, with the robot arm 20 used to support a tool or a guide, with the tool is operated by the surgeon. For example, the tooling end, also known as end effector, may be manipulated by the operator while supported by the robot arm 20. The robot arm 20 may be the coordinate measuring machine (CMM) of the tracking system 10;
- The tracking device 30 is one example of a navigation system that may optionally be used to track the patient tissue, instruments, and the robot arm 20. For example, the tracking device 30 has the capacity to capture images, e.g., in video format, using camera technology similar such as depth cameras, with optional pattern projector, as described below, or may be a different imaging technology, to provide its video feed. For example, the tracking device is a Navitrack® system having the capacity to track retroreflective elements of tracker devices on the various objects (e.g., bones, tools, implants). The tracking device 30 may be said to be stationary. In some arrangements, the tracking device 30 includes multiple points of view. For example, the tracking device 30 may include or may be embodied by a head-mounted device worn by an operator, such as by the surgeon performing surgery, as in FIG. 3. The head-mounted tracking device has the capacity to capture images. If present, the head-mounted device may have a display screen to provide data to the wearer, though this may be optional in an embodiment. The head-mounted tracking device may be used to provide a display in augmented/mixed and/or virtual reality to a user. The head-mounted tracking device may also be tasked with taking images of the surgery, with the images being used for the tracking of patient tissue (such as bones) and tools, for instance as a video feed. The head-mounted tracking device may also be used as an interface by which an operator may communicate commands to the robotic CAS system 10. The tracking device 30 may use ultrasounds as well.
- The in-robot sensor system 40 is a sensor or sensor system that uses capacitive sensing technology in order to provide some proximity sensing and other functions. The proximity sensing may be used in different ways, one of which is the generating of imaging that may then be used in tracking, as one possible use. Another contemplated use is to use the capacitive sensing technology to provide interface buttons directly on the surface of the robot arm 20. The in-robot sensor system 40 may be integrated into the robot arm 20 as shown, and may thus be said to be part of the robot. The in-robot sensor system 40 may be a native component of the robot arm 20 or may be added. Moreover, while the in-robot sensor system 40 is shown being concealed in the robot arm 20, it could be surface mounted, as a possibility. The in-robot sensor system 40 may be referred to as a sensor device, a sensor system, etc.

- The CAS controller 50 includes the processor(s) and appropriate hardware and software to run a computer-assisted surgery procedure in accordance with one or more workflows. The CAS controller 50 may include or operate the tracking module 60, and/or the robot driver 70. As described hereinafter, the CAS controller 50 may also drive the robot arm 20 through a planned surgical procedure;
- The tracking module 60 is tasked with determining the position and/or orientation of the various relevant objects during the surgery procedure, such as the bone(s) B and tool(s) T, using data acquired by the tracker device 40, as well as the data output by the in-robot sensor system 40. The tracking module 60 may also use the data from the robot arm 20, and/or obtained from the robot driver 70. The position and/or orientation may be used by the CAS controller 50 to control the robot arm 20;
- The robot driver 70 is tasked with powering or controlling the various joints of the robot arm 20, based on operator demands or on surgery planning;
- A camera may be present, for instance as a complementary registration tool. The camera may for instance be mounted on the robot arm 20, such as on the robot arm, such that the point of view of the camera is known in the frame of reference. The camera may be on its own stand as well.

Other components, devices, systems, may be present, such as surgical instruments and tools T, interfaces I/F such as displays, screens, computer station, servers, and like etc. Secondary tracking systems may also be used for redundancy.

Referring to FIG. 1, the robot 20 (referred to herein as robot 20 or robot arm 20) may have the robot arm stand from a base, for instance in a fixed relation relative to the operating-room (OR) table supporting the patient, whether it is attached or detached from the table. The robot arm 20 has a plurality of joints 21 and links 22, of any appropriate form, to support a tool head 23 that interfaces with a tool or with the patient. In FIG. 1, the tool head 23 is at the end of a distal-most link 22', also referred as wrist. The tool head 23 is shown in FIG. 1 as being a cutting guide having a slot(s) and/or drilling guide(s). The robot arm 20 is tracked to be positioned and oriented relative to a bone for alterations to be made by an operator assisted by the tool head 23 (e.g., cutting guide) or by the tool head 23 itself. For example, the end effector or tool head may optionally incorporate a force/torque sensor for collaborative/cooperative control mode, in which an operator manipulates the robot arm 20. The robot arm 20 is shown being a serial mechanism, arranged for the tool head 23 to be displaceable in a desired number of degrees of freedom (DOF). For example, the robot arm 20 controls 6-DOF movements of the tool head, i.e., X, Y, Z in the coordinate system, and pitch, roll and yaw. Fewer or additional DOFs may be present. Also, more joints 21 of different types may be present to move the tool head 23 in the manner described above. The joints 21 are powered for the robot arm 20 to move as controlled by the CAS controller 50 in the six DOFs, and in such a way that the position and orientation of the tool head 23 in the coordinate system may be known, for instance by readings from encoders on the various joints 21, or from any integrated rotational joint sensing enabling rotation of the joints 21 to be quantified. Therefore, the powering of the joints is such that the tool head 23 of the robot arm 20 may execute precise movements, such as moving along a single direction in one translational DOF, or being restricted to moving along a plane, among possibilities. Such robot arms 20 are known, for instance as described in U.S. patent application Ser. No. 11/610,728, and incorporated herein by reference.

The tool head 23 of robot arm 20 may be defined by a chuck or like tool interface, typically actuatable in rotation. As a non-exhaustive example, numerous tools may be used as end effector for the robot arm 20, such tools including a registration pointer, a reamer (e.g., cylindrical, tapered), a reciprocating saw, a retractor, a laser rangefinder or light-emitting device (e.g., the indicator device of U.S. Pat. No. 8,882,777), laminar spreader depending on the nature of the surgery. The various tools may be part of a multi-mandible configuration or may be interchangeable, whether with human assistance, or as an automated process. The installation of a tool in the tool head may then require some calibration in order to track the installed tool in the X, Y, Z coordinate system of the robot arm 20.

The tool head 23 of the robot arm 20 may also be a universal instrument adapter, which can be positioned by robot arm 20 relative to surgical area in a desired orientation according to a surgical plan, such as a plan based on preoperative imaging. The universal instrument adapter may include a tool base 23A, an extension arm 23B, at the end of which a cutting guide 24 is located. The cutting guide 24 may be known as a cutting block, adapter block, etc. In an embodiment, the extension arm 23B may have a first segment and second segment, though fewer or more segments may be present, so as to give a given orientation to the cutting guide 24 relative to the tool head 23. The cutting guide 24 may have a body defining a guide surface (e.g., cut slot), and pin holes. In an example, the cutting guide 24 can be configured as a talus resection block for use in a total knee arthroplasty. Other configurations of the cutting guide 24 may be used, such as with or without pin holes.

In order to position the cutting guide 24 or like end effector of the robot arm 20 relative to the patient B, the CAS controller 50 can manipulate the robot arm 20 automatically by the robot driver 70, or by a surgeon manually operating the robot arm 20 (e.g. physically manipulating, via a remote controller through the interface I/F) to move the end effector of the robot arm 20 to the desired location, e.g., a location called for by a surgical plan to align an instrument relative to the anatomy, with the assistance of tracking device 30 and/or of the in-robot sensor system 40.

The robot arm 20 may include sensors in its various joints 21 and links 22. The sensors may be of any appropriate type, such as rotary encoders, optical sensors, position switches, for the position and orientation of the end effector, and of the tool in the tool head 23 (e.g., cutting block 24) to be known. More particularly, the tracking module 60 may determine the position and orientation of the robot arm 20 in a frame of reference of the robot arm 20, such as by obtaining the position (x,y,z) and orientation (phi, theta, ro) of the tool from the robot driver 70 using the sensors 25 in the robot arm 20. Using the data from the sensors 25, the robot arm 20 may be the coordinate measuring machine (CMM) of the tracking system 10, with a frame of reference (e.g., coordinate system, referential system) of the procedure being relative to the fixed position of the base of the robot 20. The sensors 25 must provide the precision and accuracy appropriate for surgical procedures. The coupling of tools to the robot arm 20 may automatically cause a registration of the position and orientation of the tools in the frame of reference of the robot arm 20, though steps of calibration could be performed. For example, when the cutting guide 24 is coupled to the robot arm 20 such as in the example of FIG. 1, a position and orientation of the guide surface 24A may be registered for its subsequent tracking as the robot arm 20 moves in space. The geometry of the cutting guide 24 is thus known, as well as the manner by which the cutting guide 24 is coupled to the robot arm 20, to allow this automatic registration. Additional steps may be performed to register/calibrate the cutting guide 24, such as the contact with a probe, image processing, data entry, etc.

Figure 3:
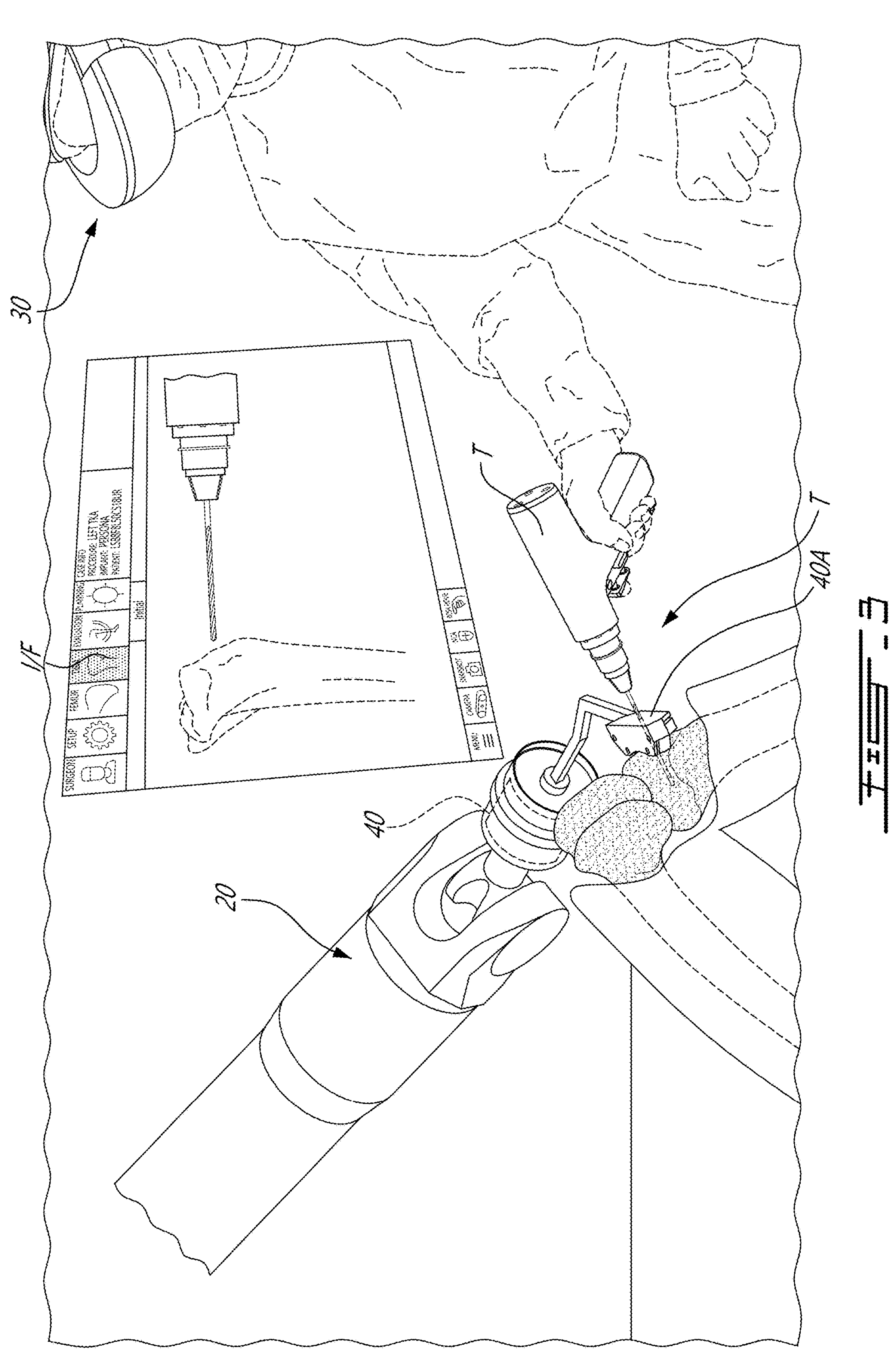
FIG. 3 is a perspective view of the surgical robot during surgery, performing skin sensing in accordance with the present disclosure.

Referring to FIG. 1B, the tracking device 30 may optionally be used to track the patient tissue, instruments, and the robot arm 20. In an embodiment, the tracking device 30 includes a Navitrack® system having the capacity to track retroreflective elements of tracker devices on the various objects (e.g., bones, tools, implants). As such, and in other variants, the tracking device 30 may have the capacity to capture images, e.g., in video format, using camera technology similar such as depth cameras, with optional pattern projector, as described below, or may be a different imaging technology, to provide its video feed. In some arrangements, the tracking device 30 includes multiple separate image capture devices from different points of view. The tracking device 30 may include or may be embodied by a head-mounted device worn by an operator, such as by the surgeon performing surgery (FIG. 3). If present, the head-mounted device may have a display screen to provide data to the wearer, though this may be optional in an embodiment.

The tracking device 30 (including the vision system of the electrical interface 40') may produce structured light illumination for tracking objects with structured light 3D imaging. In structured light illumination, a portion of the objects is illuminated with one or multiple patterns from a pattern projector or like light source. Structured light 3D imaging is based on the fact that a projection of a line of light from the pattern projector onto a 3D shaped surface produces a line of illumination that appears distorted as viewed from perspectives other than that of the pattern projector. Accordingly, imaging such a distorted line of illumination allows a geometric reconstruction of the 3D shaped surface. Imaging of the distorted line of illumination is generally performed using one or more cameras (including appropriate components such as e.g., lens(es), aperture, image sensor such as CCD, image processor) which are spaced apart from the pattern projector so as to provide such different perspectives, e.g., triangulation perspective. In some embodiments, the pattern projector is configured to project a structured light grid pattern including many lines at once as this allows the simultaneous acquisition of a multitude of samples on an increased area. In these embodiments, it may be convenient to use a pattern of parallel lines. However, other variants of structured light projection can be used in some other embodiments.

The structured light grid pattern can be projected onto the surface(s) to track using the pattern projector. In some embodiments, the structured light grid pattern can be produced by incoherent light projection, e.g., using a digital video projector, wherein the patterns are typically generated by propagating light through a digital light modulator. Examples of digital light projection technologies include transmissive liquid crystal, reflective liquid crystal on silicon (LCOS) and digital light processing (DLP) modulators. In these embodiments, the resolution of the structured light grid pattern can be limited by the size of the emitting pixels of the digital projector. Moreover, patterns generated by such digital display projectors may have small discontinuities due to the pixel boundaries in the projector. However, these discontinuities are generally sufficiently small that they are insignificant in the presence of a slight defocus. In some other embodiments, the structured light grid pattern can be produced by laser interference. For instance, in such embodiments, two or more laser beams can be interfered with one another to produce the structured light grid pattern wherein different pattern sizes can be obtained by changing the relative angle between the laser beams.

The pattern projector may emit light that is inside or outside the visible region of the electromagnetic spectrum. For instance, in some embodiments, the emitted light can be in the ultraviolet region and/or the infrared region of the electromagnetic spectrum such as to be imperceptible to the eyes of the medical personnel. In these embodiments, however, the medical personnel may be required to wear protective glasses to protect their eyes from such invisible radiations. As alternatives to structured light, the tracking device 30 may also operate with laser rangefinder technology or triangulation, as a few examples among others.

The tracking device 30 may consequently include the cameras to acquire backscatter images of the illuminated portion of objects. Hence, the cameras capture the pattern projected onto the portions of the object. The cameras are adapted to detect radiations in a region of the electromagnetic spectrum that corresponds to that of the patterns generated by the light projector. As described hereinafter, the known light pattern characteristics and known orientation of the pattern projector relative to the cameras, are used by the tracking module 60 to generate a 3D geometry of the illuminated portions, using the backscatter images captured by the camera(s). Although a single camera spaced form the pattern projector can be used, using more than one camera may increase the field of view and increase surface coverage, or precision via triangulation.

The tracking device 30 may also have one or more filters integrated into either or both of the cameras to filter out predetermined regions or spectral bands of the electromagnetic spectrum. The filter can be removably or fixedly mounted in front of any given camera. For example, the filter can be slidably movable into and out of the optical path of the cameras, manually or in an automated fashion. In some other embodiments, multiple filters may be periodically positioned in front of a given camera in order to acquire spectrally resolved images with different spectral ranges at different moments in time, thereby providing time dependent spectral multiplexing. Such an embodiment may be achieved, for example, by positioning the multiple filters in a filter wheel that is controllably rotated to bring each filter in the filter wheel into the optical path of the given one of the camera in a sequential manner.

More specifically, the filter can be used to provide a maximum contrast between different materials which can improve the imaging process and more specifically the soft tissue identification process. For example, in some embodiments, the filter can be used to filter out bands that are common to backscattered radiation from typical soft tissue items, the surgical structure of interest, and the surgical tool(s) such that backscattered radiation of high contrast between soft tissue items, surgical structure and surgical tools can be acquired. Additionally, or alternatively, where white light illumination is used, the filter can includes band pass filters configured to let pass only some spectral bands of interest. For instance, the filter can be configured to let pass spectral bands associated with backscattering or reflection caused by the bones, the soft tissue while filtering out spectral bands associated with specifically colored items such as tools, gloves and the like within the surgical field of view. Other methods for achieving spectrally selective detection, including employing spectrally narrow emitters, spectrally filtering a broadband emitter, and/or spectrally filtering a broadband imaging detector, can also be used.

Referring to FIGS. 1 to 3, the in-robot sensor system 40 is shown as being integrated into a shell of a robot arm link 22. The in-robot sensor system 40 uses capacitive sensing technology as described for example in United States Patent Application Publication No. 2020/0368924, filed on Jul. 30, 2018, by Fogale Nanotech. The in-robot sensor system 40 may thus have a plurality of capacitive electrodes that may be polarized at a first alternating electrical potential different from a ground potential at a working frequency. The in-robot sensor system 40 may have one or more guard electrodes associated with the plurality of capacitive electrode and provided to be polarized at the guard potential that is similar to the first alternating electrical potential at the working frequency. A dielectric layer(s) may be between the capacitive electrodes and the guard electrode(s). There results for example a deformable skin that may have a high distribution sensors. The deformable skin may be positioned against an inner surface of one or more of the links 22 (such as the distal link or wrist 22' as shown), such that the outer surface of the link 22 with the in-robot sensor system 40 has capacitive sensing technology.

Referring to FIG. 2, the CAS controller 50 is shown in greater detail relative to the other components of the robotized tracking system 10. The CAS controller 50 has a processor unit 51 and a non-transitory computer-readable memory 52 communicatively coupled to the processing unit 51 and configured for executing computer-readable program instructions executable by the processing unit 51 for to perform some functions, such as tracking the patient tissue and tools, using the position and orientation data from the robot 20, the readings from the tracker device unit(s) 30 and/or of the in-robot sensor system 40, depending on availability. The CAS controller 50 may also control the movement of the robot arm 20 via the robot driver module 70. The tracking system 10 may comprise various types of interfaces I/F, for the information to be provided to the operator. The interfaces I/F may include and/or screens including wireless portable devices (e.g., phones, tablets), audio guidance, LED displays, head-mounted display for virtual reality, augmented reality, mixed reality, among many other possibilities. For example, the interface I/F comprises a graphic-user interface (GUI) operated by the system 10. The CAS controller 50 may also display images captured pre-operatively, or using cameras associated with the procedure (e.g., camera, laparoscopic cameras, tool mounted cameras), for instance to be used in the collaborative/cooperative control mode of the system 10, or for visual supervision by the operator of the system 10, with augmented reality for example. The CAS controller 50 may drive the robot arm 20, in performing the surgical procedure based on the surgery planning achieved pre-operatively. The CAS controller 50 may run various modules, in the form of algorithms, code, non-transient executable instructions, etc, in order to operate the tracking system 10 in the manner described herein. The CAS controller 50 may be part of any suitable processor unit, such as a personal computer or computers including laptops and desktops, tablets, server, etc.

The tracking module 60 may be a subpart of the CAS controller 50, or an independent module or system. The tracking module 60 receives the position and orientation data from the robot 20, the readings from the tracker device 30, and from the in-robot sensor system 40. The tracking module 60 may hence determine the relative position of the objects relative to the robot arm 20 in a manner described below. The tracking module 60 may also be provided with models of the objects to be tracked. For example, the tracking module 60 may track bones and tools, and hence may use virtual bone models and tool models. The bone models may be acquired from pre-operative imaging (e.g., MRI, CT-scans), for example in 3D or in multiple 2D views, including with 2D X-ray to 3D bone model technologies. The virtual bone models may also include some image processing done preoperatively, for example to remove soft tissue or refine the surfaces that will be exposed and tracked. The virtual bone models may be of greater resolution at the parts of the bone that will be tracked during surgery, such as the knee articulation in knee surgery. The bone models may also carry additional orientation data, such as various axes (e.g., longitudinal axis, mechanical axis, etc). The bone models may therefore be patient specific. It is also considered to obtain bone models from a bone model library, with the data obtained from the video images used to match a generated 3D surface of the bone with a bone from the bone atlas. The virtual tool models may be provided by the tool manufacturer, or may also be generated in any appropriate way so as to be a virtual 3D representation of the tool(s).

Additional data may also be available, such as tool orientation (e.g., axis data and geometry). By having access to bone and tool models, the tracking module 60 may obtain additional information, such as the axes related to bones or tools.

Still referring to FIG. 2, the CAS controller 50 may have the robot driver 70. The robot driver 70 is tasked with powering or controlling the various joints of the robot arm 20. There may be some force feedback provided by the robot arm 20 to avoid damaging the bones. The robot driver 70 may perform actions based on a surgery planning. The surgery planning may be a module programmed specifically for any given patient, according to the parameters of surgery desired by an operator such as an engineer and/or surgeon. The parameters may include geometry of selected, planned bone cuts, planned cut depths, sequence or workflow of alterations with a sequence of surgical steps and tools, tools used, etc.

Now that the various components of the robotized CAS system 10 have been described, functionalities associated with the in-robot sensor system 40 are set forth, with reference to FIGS. 1, 2 and 3. The procedure shown in an exemplary embodiment is drilling a hole in a tibia to position a cutting guide thereon, the cutting guide being the tool head 23 of the robot arm 20.

One or more, or even each individual sensor of the in-robot sensor system 40 may be configured to detect an object positioned within its range of measure. Hence, one or more or even each individual sensor of the in-robot sensor system 40 can return a distance value representative of its distance from the object. With the distance measured in real-time from the sensors of the in-robot sensor system 40, the system 10 may generate a point cloud representative of the surface of the object detected by at least some of the sensors of the in-robot sensor system 40. Accordingly, the in-robot sensor system 40 may generate a 3D surface model of the object (i.e., the 3D model of the outer surface of the object) such as via a processing unit thereof, or through the processing capacity of the CAS controller 50 (e.g., via the tracking module 60). Hence, the system 10 may digitize objects that are within the range of detection of the in-robot sensor system 40. The resolution of the cloud depends to the density of sensors the in-robot sensor system 40. A high density of sensors will provide the best resolution.

Using real-time information returned from the in-robot sensor system 40, the CAS controller 50 may know the distance of objects relative to the robot arm 20. With this distance data returned by each sensor of the in-robot sensor system 40, the CAS controller 50 may scan an object, such as by 3D scanning. The scanning mode can be used when the robot arm 20 is stationary or when the robot arm 20 moves. This functionality can be used to scan the patient anatomy at given moments or throughout a surgical procedure. Therefore, the in-robot sensor system 40 may be used by the CAS controller 50 to perform anatomical registration preoperatively, intraoperatively or postoperatively, and this may be done in a continuous manner. The registration may be defined as the locating a tracked object(s) such as a bone and tool, in a common referential system.

As another possible navigation functionality, the CAS controller 50 may operate a dedicated control loop, by which the CAS controller 50 commands the robot arm 20 to move for example to keep a fixed distance between itself and an object, or the CAS controller 50 blocks movement of the robot arm 20 when in a collaborative mode. For example, with this functionality, the robot arm 20 may be driven to move in real time to compensate for movement of the patient anatomy. This functionality could be used for soft tissue or hard tissue.

As another possible navigation functionality, the CAS controller 50 may operate a collaborative mode, i.e., a mode in which manipulations of the operator are used to displace the robot arm, but without an actual physical touch of the robot arm 20. When such a mode is selected and operated by the CAS controller 50, the in-robot sensor system 40 detects the proximity of the operator's hand (or other body part), and moves as a function of the displacement of the operator's hand, with the CAS controller 50 using the robot driver module 70 to actuate the motorized joints 21 to cause the movement. Because the in-robot sensor system 40 may have the capacity to model objects, the CAS controller 50 may require a given hand shape (e.g., pointing finger) to authorize the movement in the collaborative mode. This is merely an option.

To assist in the scanning of the object(s) with the in-robot sensor system 40, a calibrated object may be used as reference, to check the accuracy of the scanning by the in-robot sensor system 40, and/or to calibrate the in-robot sensor system 40 and/or bring adjustments to the readings. The position and the orientation of the reference object may be calibrated for instance using a 3D CMM (coordinate measurement machine), to contribute to the accuracy of the navigating. An optimization algorithm may be part of the readable instructions 52, compute a registration between the reference and the measurement. A rms error value may be indicative of the accuracy of the in-robot sensor system 40, and may be an additional functionality to automatically verify the accuracy of the system 40 before to start the surgery.

With this 3D scanning functionality, the CAS controller 50 may track the object(s). After an initialization step to scan an object in a fixed position, the initial position and the orientation of the object may be determined using the 3D scanning, and this may be completed by the use of an existing 3D model of the object(s). Moreover, if the tracking device 30 is present, the 3D scanning with the in-robot sensor system 40 may be used as a redundant, secondary or primary tracking feed. If the object is moved, the feed from the in-robot sensor system 40 may be used to perform tracking in real-time of the current position and orientation of the object(s). The data from the in-robot sensor system 40 can be used as a GPS-like signal, also providing visual feedback for the surgeon if desired, for the surgeon and/or operating room staff to see in real-time the position of an instrument relative to the current position of the patient (e.g., bone of a patient). The use of the in-robot sensor system 40 to navigate (i.e., track) object(s) may be ergonomically desired, as the in-robot sensor system 40 may be embedded into the robot arm 20 and thus does not occupy any additional sterile field space.

If the object tracked is an object known by the CAS controller 50, such as a given tool or a bone having been modeled three-dimensionally virtually with a different imaging modality (e.g., MRI, radiography), the tracking module 60 may map the detected 3D surface model to such an existing model of the known object. In such a scenario, the detecting performed by the in-robot sensor system 40 contributes to the tracking of objects, by providing additional tracking data to that provided by the tracker device 30. For example, if the tracker device 30 is an optical tracking device as suggested above as an option, the line of sight between the tracker device 30 and the object may be temporarily disrupted (e.g., interference of a human staff). The object detecting performed by the in-robot sensor system 40 may be used to ensure that the tracking feed is continuous, in spite of a disruption of tracking by the tracker device 30. This is one possibility among others.

In any contemplated use, it bears mentioning that the robot arm 20 is often covered by a surgical drape, except for the end effector, tool head 23, and possibly part of the distal link 22'. The surgical drape is often a transparent plastic cover for sterilization of the surgical workspace. Unlike some other sensor technologies, the in-robot sensor system 40 uses capacitive sensing that can perform object detection in spite of the presence of the surgical drape (if present).

Using real-time information returned from the in-robot sensor system 40, the CAS controller 50 may determine the distance of objects within the range of sensors of the in-robot sensor system 40. Object is a generic term for any component in the surgical environment of the robotic arm 20 during surgery, such as instruments, anatomical features of a patient (e.g., bone), operating table, nurse, surgeon, patient camera, lights, etc. Capacitive sensing allows in-robot sensor system 40 to detect obstacles before to contact is made.

In an embodiment, the in-robot sensor system 40 is used to define interface points on the robot arm 20. For example, stickers or like visual indicators may be positioned on the shell of the link 22 or 22', in zones with coverage by the in-robot sensor system 40. The zones may be configured in the CAS system 10 for a touch of the sticker or like visual indicator to be interpreted as a "mouse click" or like interface signal from the user to the robot arm 20. Stated differently, such stickers or visual indicators may be virtual buttons directly onto the robot arm 20 to detect interactions coming from the user. The operator may be asked to perform a configuration procedure to configure such virtual buttons, such that the configuration may be customized according to an operator's preferences. The expression "virtual button" is used to describe the fact that the stickers or visual indicators are not active in and of themselves, but they are virtually active, i.e., the system 10 detects proximity and/or contact with these stickers and visual indicators and will virtually (numerical) active an action. The stickers, visual indicators or any other form of these virtual buttons are passive, and will be used to trigger an action as a result of a virtual signal interpretation by parts of the system 10.

As the in-robot sensor system 40 and CAS controller 50 may have the capacity to determine a distance and/or to generate a model surface of the object, the in-robot sensor system 40/CAS controller 50 may be programmed to accept an interface command through such virtual buttons only if some conditions are met. The programming may be done intraoperatively, i.e., a user may position a passive visual indicator and program the action associated with the triggering of this passive visual indicator. For example, it may be required that the surface of the robot arm 20 be touched or that a finger may be brought to a given close proximity (within a proximity distance of the robot arm 20), for the CAS controller 50 to trigger an interaction (e.g., a mouse click). The proximity distance may, for example, be 2.0 cm or less from the proximity distance, or even in direct contact with the zone (i.e., the passive visual indicator). As another example, the in-robot sensor system 40/CAS controller 50 may process the point cloud to ensure that a finger (or two fingers, or a thumb, just to name a few examples) or other body member is used to trigger an interaction with the virtual button, for example to discriminate an actual button trigger from an accidental contact by an instrument, or forearm. A prolonged contact or proximity of the finger or other body member may be used as a "clickhold", as if a mouse button were held down.

Examples of virtual buttons may be that of a collaborative mode as explained above, and this includes a contactless collaborative mode. The activation of this mode allows the operator to guide movements of the robot arm 20 via the detection of the user's hand or other body part by the in-robot sensor system 40. The collaborative mode may be with contact or without contact.

Another virtual button may be a home button, by which the robot arm 20 may automatically return to a given base position.

Yet another virtual button may be a stop or pause button, by which the robot arm 20 is stopped or paused from performing an action, from moving along a given trajectory.

Yet another virtual button is an automatic mode button, according to which the user must use an interface to control movement of the robot arm 20.

Yet another virtual button may be a mouse pad zone, with the operator having the possibility of moving a virtual pointer as if the operator were manipulating a mouse.

There are a few examples of virtual buttons that may be configured, using the feed from the in-robot sensor system 40 to enable them. If there are multiple ones of such zones, the user interaction of a first type may be triggered when the object is within a proximity distance to a first of the passive visual indicators, and the user interaction of a second type may be triggered when the object is within a proximity distance to a second of the passive visual indicators.

The interactions with the in-robot sensor system 40/CAS controller 50 may as a result reduce the number of interactions with a touchscreen from the interfaces I/F, and may allow the surgeon to remain focused on the surgical field instead of looking at a touchscreen. Using the in-robot sensor system 40 in the manners described above, the user experience may be enhanced, notably by reducing the number of touches on a touchscreen, and by potentially reducing the time of the surgical procedure.

The use of the in-robot sensor system 40 as described above may contributing to solving some problems associated with the use of robot arms in surgery. For example, the in-robot sensor system 40 may facilitate robot/user interactions. The in-robot sensor system 40 may be used to provide an efficient, non-invasive, and contactless method for 3D acquisition of patient anatomy in order to perform registration between the robot 20, the patient and instruments with a referential system of the surgery. It may also be used to define a non-invasive and contactless patient and object tracking method, whether in collaboration with another tracking system (e.g., tracking device 30) or independently.

The invention claimed is:

1. A robotized computer-assisted surgery system, comprising:

a robot arm;

an in-robot sensor system in the robot arm, the in-robot robot system having a plurality of capacitive sensors;

a processing unit; and a non-transitory computer-readable memory communicatively coupled to the processing unit and comprising computer-readable program instructions executable by the processing unit for:

obtaining readings from at least some of the plurality of capacitive sensors representative of at least one object within range;

generating a surface model of the at least one object from the readings; and continuously tracking and outputting the position and orientation of the at least one object relative to the robot arm, using the readings and the surface model.

2. The robotized computer-assisted surgery system according to claim 1, wherein the computer-readable program instructions are executable by the processing unit for controlling movements of the robot arm as a function of a position and orientation of the surface model of the at least one object.

3. The robotized computer-assisted surgery system according to claim 1, wherein the surgery system is configured to perform the continuously tracking and outputting the position and orientation solely with the in-robot sensor system.

4. The robotized computer-assisted surgery system according to claim 1, wherein the surgery system includes a tracker device for optically tracking the at least one object and the robot arm, the surgery system is configured to perform the continuously tracking and outputting the position and orientation with the in-robot sensor system and with readings from the tracker device.

5. The robotized computer-assisted surgery system according to claim 1, wherein the plurality of capacitive sensors are concealed within the robot arm.

6. The robotized computer-assisted surgery system according to claim 1, wherein the at least one object is at least one anatomical part of a patient.

7. The robotized computer-assisted surgery system according to claim 1, wherein the surgery system is configured to block movement of the robot arm to avoid contact with the at least one object, using the tracking of the at least one object.

8. The robotized computer-assisted surgery system according to claim 1, wherein the surgery system is configured to output an image of the surface model of the at least one object.

9. The robotized computer-assisted surgery system according to claim 8, wherein the surgery system is configured to output an image of a tool supported by the robot arm relative to the image of the surface model of the at least one object.

10. A robotized computer-assisted surgery system, comprising:

a robot arm;

an in-robot sensor system in the robot arm, the in-robot robot system having a plurality of capacitive sensors, the plurality of capacitive sensors are concealed within the robot arm;

a processing unit; and a non-transitory computer-readable memory communicatively coupled to the processing unit and comprising computer-readable program instructions executable by the processing unit for:

obtaining readings from at least some of the capacitive sensors representative of at least one object within range of the capacitive sensors;

processing the readings to determine a location of the at least one object relative to the robot arm; and triggering a user interaction with the robotized computer-assisted surgery system when the at least one object is at a given location relative to the robot arm.

11. The robotized computer-assisted surgery system according to claim 10, wherein the computer-readable program instructions are executable by the processing unit for triggering the user interaction by activating a collaborative mode, in which the robot arm is configured to move based on movements of the user as detected by some of the plurality of capacitive sensors.

12. The robotized computer-assisted surgery system according to claim 10, wherein the computer-readable program instructions are executable by the processing unit for triggering the user interaction as a movement of a mouse on a pad by the at least one object moving relative to a given zone of the robot arm.

13. The robotized computer-assisted surgery system according to claim 10, wherein the at least one object is a user's hand.

14. The robotized computer-assisted surgery system according to claim 10, wherein the computer-readable program instructions are executable by the processing unit for triggering the user interaction with the robotized computer-assisted surgery system when the at least one object is within a proximity distance of part of the robot arm.

15. The robotized computer-assisted surgery system according to claim 14, wherein the computer-readable program instructions are executable by the processing unit for triggering the user interaction when the at least one object is within a proximity distance to a passive visual indicator on the robot arm.

16. The robotized computer-assisted surgery system according to claim 15, wherein the computer-readable program instructions are executable by the processing unit for triggering the user interaction when the at least one object touches the passive visual indicator on the robot arm.

17. The robotized computer-assisted surgery system according to claim 15, wherein the computer-readable program instructions are executable by the processing unit for associating a type of interaction associated with the passive virtual indicator.

18. The robotized computer-assisted surgery system according to claim 15, including at least two of the passive visual indicator.

19. The robotized computer-assisted surgery system according to claim 18, wherein the computer-readable program instructions are executable by the processing unit for triggering the user interaction of a first type when the at least one object is within a proximity distance to a first of the at least two passive visual indicators, and for triggering the user interaction of a second type when the at least one object is within a proximity distance to a second of the at least two passive visual indicators.

* * * * *